(12) United States Patent
Bonnard et al.

(10) Patent No.: US 6,699,988 B2
(45) Date of Patent: Mar. 2, 2004

(54) PROCESS FOR THE PREPARATION OF N,N'-CARBONYLBISLACTAMS

(75) Inventors: Hubert Bonnard, Cerny (FR); Laurence Ferruccio, Vert le Grand (FR); Jean-Pierre Senet, Buthiers (FR); Pierre-Yves Le Roy, Roques sur Garonne (FR)

(73) Assignee: SNPE, Paris Cedex (FR)

( * ) Notice: Subject to any disclaimer, the term of this patent is extended or adjusted under 35 U.S.C. 154(b) by 60 days.

(21) Appl. No.: 09/840,388

(22) Filed: Apr. 23, 2001

(65) Prior Publication Data

US 2001/0044532 A1 Nov. 22, 2001

(30) Foreign Application Priority Data

Apr. 28, 2000 (FR) .............................................. 00 05502

(51) Int. Cl.[7] .............................................. C07D 223/10
(52) U.S. Cl. ....................................................... 540/525
(58) Field of Search ......................................... 540/525

(56) References Cited

U.S. PATENT DOCUMENTS 5,972,237 A   10/1999   Müller et al. .......... 252/186.39

FOREIGN PATENT DOCUMENTS

JP         17832        1/2000

OTHER PUBLICATIONS

CA 52: 11781e (1956), H.R. Meyer.
Polymer Journal, vol. 27, No. 5, pp 449–460 (1995), Mateva et al.

*Primary Examiner*—Bruck Kifle
(74) *Attorney, Agent, or Firm*—Bucknam & Archer

(57) ABSTRACT

The invention relates to a process for the preparation of N,N'-carbonylbislactams by reaction of phosgene with at least one lactam which is characterized in that the tertiary amine is chosen from the group consisting of non-nucleophilic aliphatic tertiary amines. N,N'-Carbonylbislactams of high purity are thus obtained with good yields, both in the laboratory and on the industrial scale.

13 Claims, No Drawings

PROCESS FOR THE PREPARATION OF N,N'-CARBONYLBISLACTAMS

The invention relates to the preparation of N,N'-carbonylbislactams. It relates in particular to an improved process for the preparation of the latter from lactams and phosgene.

Processes for the preparation of N,N'-carbonylbislactams are not very numerous. Phosgene is used in most of them. The second reactant is then a lactam or one of its derivatives, such as an alkaline salt or a trimethylsilyl derivative. None of these processes is satisfactory.

Thus, when phosgene is reacted with the sodium salt of ε-caprolactam according to H. R. Meyer, as described in the summary CA 52: 11781e of 1956, only from 0.6 to 40% of N,N'-carbonylbiscaprolactam is obtained.

According to another method, as described in the article CA 68: 104571, ε-caprolactam and phosgene are reacted in the presence of a non-protonic amine, such as triethylamine, at a temperature of 20° C. and then to 40° C. The yield on the laboratory scale would be slightly higher, approximately 60%. However, when this example is repeated, the yield obtained is only 40%. Furthermore, if larger amounts of reactants are used, for example suitable for a 50-liter reactor, the yield is then only 23%.

In U.S. Pat. No. 5,972,237, the same method for the preparation of N,N'-carbonylbiscaprolactam is employed. The amine used is dimethylcyclohexylamine. The yield indicated is then only 46%.

According to another process (Polymer Journal, 1995, 27(5), pp. 449–450), first of all the N-trimethylsilyl derivative of ε-caprolactam is formed and then a portion of the latter is reacted with phosgene to form the carbamoyl chloride. The two intermediate compounds are subsequently reacted with one another to produce the carbonylbiscaprolactam. Three stages are consequently needed. The yield is not mentioned. When this procedure is repeated, a yield of 51% is found.

N,N'-Carbonylbislactams are very useful compounds, in particular as cocatalysts and activators in the manufacture of polymers, such as polyamides or polyesters, as activators of inorganic peroxides in detergents or as intermediates in the synthesis of amino acids. For most of their applications, they have to be of high purity.

There consequently existed a need to produce N,N'-carbonylbislactams with a good yield, not only in the laboratory but also on an industrial scale, and under economical conditions.

Another object of the present invention is to obtain them with high purity.

The process according to the invention solves the problems indicated above. It consists in reacting phosgene with at least one lactam in the presence of a tertiary amine chosen from the group consisting of non-nucleophilic aliphatic tertiary amines.

N,N'-Carbonylbislactams are obtained by virtue of this process generally with a yield of greater than 70% and a purity of greater than 99%.

The process is particularly advantageous for converting lactams of formula (I):

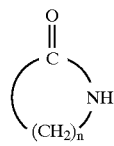

in which n represents an integer from 3 to 15 and preferably from 5 to 12.

The N,N'-carbonylbislactams obtained have the formula (II):

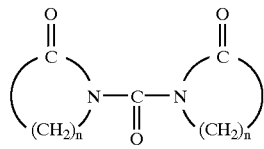

When a single lactam is used, both rings of the compound are identical. When several different lactams are used as starting compounds, a mixture of N,N'-carbonylbislactams with identical or different rings is obtained.

Phosgene is reacted with the lactam or lactams generally in a stoichiometric amount or an amount close to this value, i.e. approximately 0.5 mol of phosgene per mole of lactam. A large molar excess of phosgene is not necessary. Preferably, from 0.5 to 0.55 mol of phosgene is used per mole of lactams.

In a particularly unexpected way, it has been found that the nature of the amine was very important in solving the problems which were posed in the production of N,N'-carbonylbislactams under good conditions.

The amine has to be selected from aliphatic tertiary amines which are non-nucleophilic or virtually non-nucleophilic, that is to say which are unreactive or virtually unreactive with respect to electrophilic entities, such as, for example, the carbonyl group. These amines are generally amines having very bulky radicals which thus prevent the free electron doublet of nitrogen from being accessible.

It is preferable for the amines also to be highly basic.

The useful amines are in particular amines of formula $NR^1R^2R^3$ in which $R^1$ represents the methyl or ethyl radical while $R^2$ and $R^3$, which are identical or different, represent the isopropyl or isobutyl radical. Mention may be made, as examples of such amines, of diisopropylmethylamine, diisopropylethylamine or diisobutylethylamine. Use is preferably made of diisopropylethylamine.

The presence of an amount of amine sufficient to trap the hydrochloric acid which is formed during the reaction is necessary. Use is generally made of approximately 1 mol of amine per mole of lactam and preferably of 0.95 to 1.05 mol per mole of lactam. An excess of amine is pointless.

According to the abovementioned processes of the prior art in which phosgene is used, the latter is introduced into the reaction medium at a temperature of approximately 20° C. It has now been found that the process according to the invention is further improved by introducing the phosgene into the reaction medium at a temperature of between approximately −10° C. and +5° C. and preferably of between approximately −5° C. and 0° C. The yields are better and the purity even higher. The introduction of phosgene generally lasts one to several hours.

The reaction is generally carried out in an organic solvent which is inert with respect to the reactants and which has a melting point below the temperature for introduction of the phosgene, in particular below approximately −10° C. The boiling point of the solvent is preferably less than approximately 160° C. Aromatic solvents, such as toluene and xylene, are highly suitable.

When all the amount of phosgene has been introduced, the reaction is allowed to continue at a temperature of approximately 40° to 50° C., generally for a few hours.

To recover the N,N'-carbonylbislactams obtained, the amine hydrochloride which is formed is generally separated from the medium, for example by filtration or by washing with water followed by the recovery of the aqueous phase by separation by settling, and then the solvent is removed, in particular by evaporation under reduced pressure. A compound which is not a solvent for carbonylbislactams, such as isopropanol, methanol or water, can optionally then be added to the medium and then the carbonylbislactams are precipitated. If necessary, they can furthermore be purified by washing with an alcohol, such as, for example, methanol, and/or a recystallization can be carried out.

The yields obtained by virtue of the process of the invention are markedly improved with respect to those of the prior art. Thus, N,N'-carbonylbiscaprolactam can be obtained with a yield in the laboratory of greater than 80% and on the industrial scale of greater than 70%. The purity is excellent and generally greater than 99%.

The process according to the invention is particularly economical because a means has also been found for recovering the diisopropylethylamine with a high purity from its hydrochloride formed during the reaction. To do this, an aqueous solution of the amine hydrochloride with water, preferably very pure water, is formed, either after having separated the hydrochloride from the reaction medium or by adding water to the medium and by recovering the aqueous phase, for example by separating by settling, and then this solution is neutralized with an inorganic alkaline base, such as lithium hydroxide, sodium hydroxide or potassium hydroxide, in particular in aqueous solution. Sodium hydroxide is the preferred base.

Use is generally made of an amount of base such that the final pH of the solution is approximately 13.

A codistillation of the solution is then carried out, generally at a temperature of between approximately 83° C. and approximately 91° C. at standard pressure. The amine is separated by settling from the mixture recovered. It generally has a purity, determined by GC analysis, equal to or greater than 99% and can be used in a further cycle for the production of N,N'-carbonylbislactams.

The examples which follow illustrate the invention without, however, limiting it.

EXAMPLE 1

Preparation of N,N'-carbonylbis(ε-caprolactam) (Denoted CBC)

2.1 kg of toluene, 277 g (2.426 mol) of ε-caprolactam and 318 g (2.43 mol) of diisopropylethylamine (denoted DIEA) are introduced into a jacketed reactor equipped with a mechanical stirrer rotating at 300 rev/min. The mixture is cooled to −5° C. and 129 g (1.3 mol) of gaseous phosgene are steadily introduced into the mixture at a flow rate of approximately 75 g per hour, the temperature being maintained between −5° C. and 0° C.

On completion of the introduction of the phosgene, the reaction medium is heated to 40°–43° C. and is maintained at this temperature with stirring for 5 h.

It is subsequently cooled to approximately +10° C. and then the precipitate formed is separated by filtration. The cake is rinsed with 499 g and then 402 g and 491 g of toluene. 447.9 g of wet DIEA hydrochloride are then recovered.

The filtrates obtained are combined and constitute a single toluene phase of 3.629 kg. The mixture is then concentrated by distilling off 3.029 kg of toluene at 35° C. under 14–25 mm of Hg. The CBC precipitates during the distillation but the medium remains stirrable.

1.8 kg of isopropanol are then added to the medium and 1.875 kg of an isopropanol/toluene (84/16 by mass) mixture are distilled off at 62°–43° C. under 381 to 133 mm of Hg.

The medium is subsequently heated to 76° C. and the CBC redissolves. The solution is cooled to 0°–5° C. and the CBC precipitates at approximately 45° C.

The mixture is filtered and the cake is washed with 53 g and then 47 g of isopropanol at 0°–5° C. The large white crystals obtained are subsequently dried in an oven under reduced pressure (10 mm Hg, 70° C.) for 1 hour.

248 g of N,N'-carbonylbis(ε-caprolactam) (81% yield with respect to the starting ε-caprolactam) are thus obtained with a purity of 100% (HPLC quantitative determination) and with an undetectable content of chloride, thus demonstrating the absence of troublesome products, such as the carbamoyl chloride or organic salts of Vilsmeier-Haack type.

EXAMPLE 2

Preparation of N,N'-carbonylbis (ε-caprolactam)

The preparation is carried out as in Example 1 but using 300 ml of toluene, 0.402 mol of ε-caprolactam, 0.404 mol of DIEA and 0.21 mol of phosgene and introducing the phosgene over 30 min while maintaining the temperature of the reaction medium between 10° C. and 17° C.

N,N'-Carbonylbis(ε-caprolactam) is obtained with a yield of 77% and a purity of 98% (HPLC quantitative determination).

COMPARATIVE EXAMPLE

Preparation of N,N'-carbonylbis(ε-caprolactam) by Phosgenation in the Presence of Triethylamine.

The preparation is carried out as in Example 2 but replacing DIEA with 0.42 mol of triethylamine N,N'-Carbonylbis(ε-caprolactam) is then obtained with a yield of only 14% and a purity of 95% (HPLC quantitative determination).

EXAMPLE 3

Preparation of N,N'-carbonylbis(ε-caprolactam)

The preparation is carried out as in Example 1 but using 400 ml of toluene, 0.403 mol of ε-caprolactam, 0.404 mol of DIEA and 0.25 mol of phosgene.

N,N'-Carbonylbis(ε-caprolactam) is obtained with a yield of 70% and a purity of 98% (HPLC quantitative determination).

EXAMPLE 4

Recovery and Recycling of the Diisopropylethylamine Used in Example 1

95 g of distilled water and 145.7 g (0.87 mol) of DIEA hydrochloride obtained in Example 1 are introduced into a 0.5 l jacketed reactor equipped with a Dean and Stark apparatus for recycling of the lower phase and with a coiled distillate-tube condenser fed with glycol at −15° C. Dissolution of the hydrochloride is complete in 15 min at 20° C.

114 g (0.914 mol) of a 32% aqueous sodium hydroxide solution are then added. Neutralization is endothermic. The final pH of the solution is adjusted to 13±0.5.

Codistillation is carried out at a temperature of 83°–91° C. (pot temperature 103°–109° C.) at standard pressure. A mixture composed of an aqueous phase (87 g) and of DIEA is then obtained, which separates by settling. 111.3 g of DIEA with a purity of 99% (GC analysis), comprising 0.14% of water and not comprising diisopropylamine, are thus recovered. The yield is 98% with respect to the starting DIEA hydrochloride.

This DIEA is used to prepare CBC according to the procedure of Example 1. N,N'-Carbonylbis(ε-caprolactam) is then obtained with a yield of 83% and a purity of greater than 99.7% (HPLC quantitative determination).

EXAMPLE 5

Preparation of N,N'-carbonylbis(ε-caprolactam)

2.2 kg of ε-caprolactam (19.4 mol) are suspended in 6.6 kg of toluene (i.e. a caprolactam concentration of 25%) in a stirred 20 l reactor. 2.59 kg of diisopropylethylamine (DIEA, 20.0 mol, 1.03 eq) are subsequently added at ambient temperature. The medium is cooled to 0° C. and 1.0 kg of gaseous phosgene (10.1 mol, 0.52 eq) are then introduced into the medium, the temperature of the reactor remaining below 12° C. On completion of the introduction, the medium is heated at 40°–50° C. for two hours and then 4.4 kg of water are added to the medium over 30 minutes between 50° and 40° C. The DIEA hydrochloride immediately dissolves. After stirring for 30 minutes, the stirring is halted and the homogeneous phases are separated by settling for 30 minutes. The aqueous phase (7.8 kg) is withdrawn and stored for reprocessing of the DIEA hydrochloride. The toluene phase is heated and placed under vacuum in order to carry out the concentrating (at 35°–50° C. under 80–50 mmHg). 4.8 kg of toluene are distilled off over 1.5 hours and then the vacuum is broken and 5 kg of water are run into the medium. The CBC crystallizes. The reactor is again placed under vacuum (at 65°–70° C. under 450–400 mmHg) in order to distil off the water/toluene azeotrope for the purpose of thoroughly removing toluene from the medium. After distilling for 3.5 h, 960 g of toluene and 140 g of water are recovered in the distillates. 4.8 kg of methanol are then added to the medium at atmospheric pressure and the medium is stirred for 1 h at 40° C. It is subsequently cooled to 5° C. and the suspension is conveyed onto the filter. 8.4 kg of mother liquors are recovered and the cake is washed with 2.5 kg of a 50/50 mixture of water and methanol (2.55 kg of wash liquors are recovered). 1.9 kg of wet CBC are isolated on the filter. After drying for 6 h (at 50° C. under 10 mmHg), 1.85 kg (76% yield) of dry CBC are obtained with a purity of greater than 99.5% (% w/w, HPLC) and with a melting point of 115° C.

What is claimed is:

1. Process for the preparation of N,N'-carbonylbislactams comprising
    reacting phosgene with at least one starting lactam in the presence of a tertiary amine,
    wherein the tertiary amine is selected from the group consisting of non-nucleophilic aliphatic tertiary amines of formula $NR^1R^2R^3$ in which $R^1$ represents the methyl or ethyl radical and $R^2$ and $R^3$, which are identical or different, represent the isopropyl or isobutyl radical, and
    wherein the starting lactams are represented by the general formula (I):

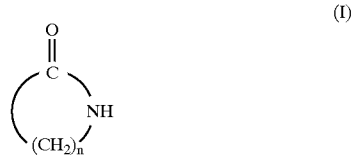

in which n represents an integer 3, 4 or 5.

2. Process according to claim 1,
    wherein the amine is diisopropylethylamine.
3. Process according to claim 1,
    wherein phosgene is introduced into a reaction mixture at a temperature of between approximately −10° C. and approximately +5° C.
4. Process according to claim 2,
    wherein phosgene is introduced into a reaction mixture at a temperature of between approximately −10° C. and approximately +5° C.
5. Process according to claim 3,
    wherein after the introduction of the phosgene, the reaction mixture is heated at a temperature of between approximately 40° and approximately 50° C.
6. Process according to claim 4,
    wherein after the introduction of the phosgene, the reaction mixture is heated at a temperature of between approximately 40° and approximately 50° C.
7. Process according to claim 3,
    wherein the reaction is carried out in a solvent chosen from solvents with a melting point below approximately −10° C.
8. Process according to claim 4,
    wherein the reaction is carried out in a solvent chosen from solvents with a melting point below approximately −10° C.
9. Process according to claim 2,
    wherein on completion of the reaction, in order to recover the diisopropylethylamine, the diisopropylethylamine hydrochloride formed is dissolved in water by adding water to the reaction mixture or after having separated the hydrochloride from the mixture the aqueous solution obtained, if appropriate separated from the reaction mixture is neutralized with an inorganic alkaline base and then codistillation of the mixture is carried out.
10. Process according to claim 9,
    wherein the amount of base added is such that the final pH is approximately 13.
11. Process according to claim 9,
    wherein the codistillation temperature is between approximately 83° C. and 91° C.
12. Process according to claim 1,
    wherein the N,N'-carbonylbislactam is recovered by crystallization from water.
13. Process according to claim 1,
    wherein the N,N'-carbonylbislactam is purified by washing with an alcohol.

* * * * *